United States Patent [19]

Rook et al.

[11] 4,392,746
[45] Jul. 12, 1983

[54] PORTABLE PHOTOMETER

[75] Inventors: Graham A. W. Rook, London; Colin H. Cameron, Chatham, both of England

[73] Assignee: Portalab Instruments Limited, London, England

[21] Appl. No.: 214,530

[22] Filed: Dec. 8, 1980

[51] Int. Cl.³ ............................................ G01N 21/27
[52] U.S. Cl. .................................................... 356/409
[58] Field of Search ............... 356/432, 435, 440, 409, 356/411, 414, 419, 420

[56] References Cited

U.S. PATENT DOCUMENTS

| | | | |
|---|---|---|---|
| 3,580,683 | 5/1971 | Schulkind | 356/414 |
| 3,910,701 | 10/1975 | Henderson et al. | 356/73 |
| 4,003,662 | 1/1977 | Retzer et al. | 356/435 |
| 4,193,694 | 3/1980 | Smith | 356/411 |

FOREIGN PATENT DOCUMENTS 7031864 3/1971 Fed. Rep. of Germany
1,486,210 9/1977 United Kingdom.

Primary Examiner—Bruce Y. Arnold
Attorney, Agent, or Firm—Watson, Cole, Grindle & Watson

[57] ABSTRACT

A portable photometer comprises a vertically movable collimator assembly arranged to depend into one of a plurality of liquid sample receiving containers provided in a tray which is movable in two horizontal directions. The collimator assembly and tray are covered in use by a movable cover movement of which causes the vertical movement of the collimator assembly. A light emitting diode is mounted in the assembly together with a collimator to ensure that only a narrow beam of light is emitted which will not impringe on the sides of the container. The assembly is also provided with a locating member for engagement with the tray to ensure that the tip of the collimator is an accurately defined distance from the bottom of the collimator. The light passing through a solution is detected by a photo detector located below the tray and in register with the light emitting diode and collimator assembly.

5 Claims, 5 Drawing Figures

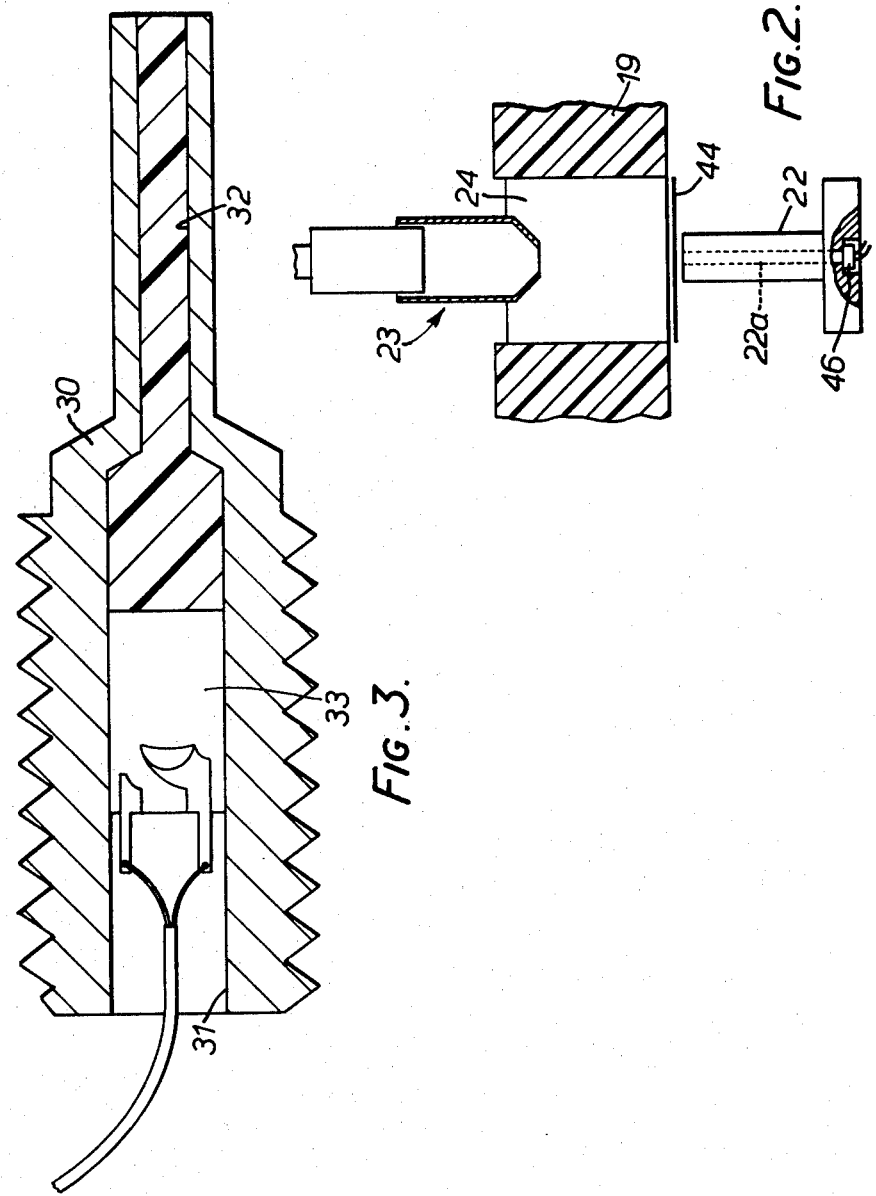

PORTABLE PHOTOMETER

The present invention relates to a photometer.

Photometers are well known instruments used for indicating the luminous intensity of sources of light. Much work has been done to make photometers useful laboratory instruments but this work has involved making the photometers very large, heavy, complicated and expensive. Laboratory photometers, in addition to being complicated also require to be mains operated.

The present invention provides a photometer comprising a monochromatic light source selected to give a desired fixed wavelength, a photodetecting device mounted in register with the light source but spaced apart by a predetermined distance, and means for enabling a sample to be tested to be brought into the space between the light source and detecting device.

Preferably, the light source is a light emitting diode.

An advantage of the present invention is that it can be made portable by using either a battery or a mains powered adaptor as the power source.

Features and advantages of the present invention will become apparent from the following description of an embodiment thereof, given by way of example with reference to the accompanying drawings, in which:

FIG. 2 is a diagrammatic side view of a portion of the photometer shown in FIG. 1.;

FIG. 3 is a sectional side view of a light source and collimator assembly used in the photometer shown in FIG. 1;

A number of laboratory assays, in particular the Enzyme Linked Immunosorbent Assay, at present require expensive mains operated apparatus capable of measuring absorbance of solutions at defined wavelengths.

We describe a simple battery-operated photometer which incorporates a monochromatic light source of fixed intensity and wavelength such as a light emitting diode (L.E.D.). The L.E.D. is mounted in a collimator which is inserted a few millimeters into the test solution. In the prototype this solution is contained in the wells of flat bottomed Dynatech Microelisa trays. The collimator/L.E.D. assembly can be centred and adjusted for height.

The collimator gives a restricted beam which does not impinge on the sides of the microtitre wells. The beam passes through the solution and through the flat bottom of the well and hits a diffuser made from white plastic sheet. This diffuser is rigidly mounted in an assembly a few millimeters above the light sensitive portion of the photodiode. The diffuser/photodiode assembly may be spring mounted so that the diffuser of the assembly is always in contact with the bottom of the well or else it can be provided with a collimator and fixed in position. The fixed position is shown diagrammatically in FIG. 2 in which the photodiode is referenced 46, the collimator is referenced 22a and the diffuser is referenced 44.

Figure 1:
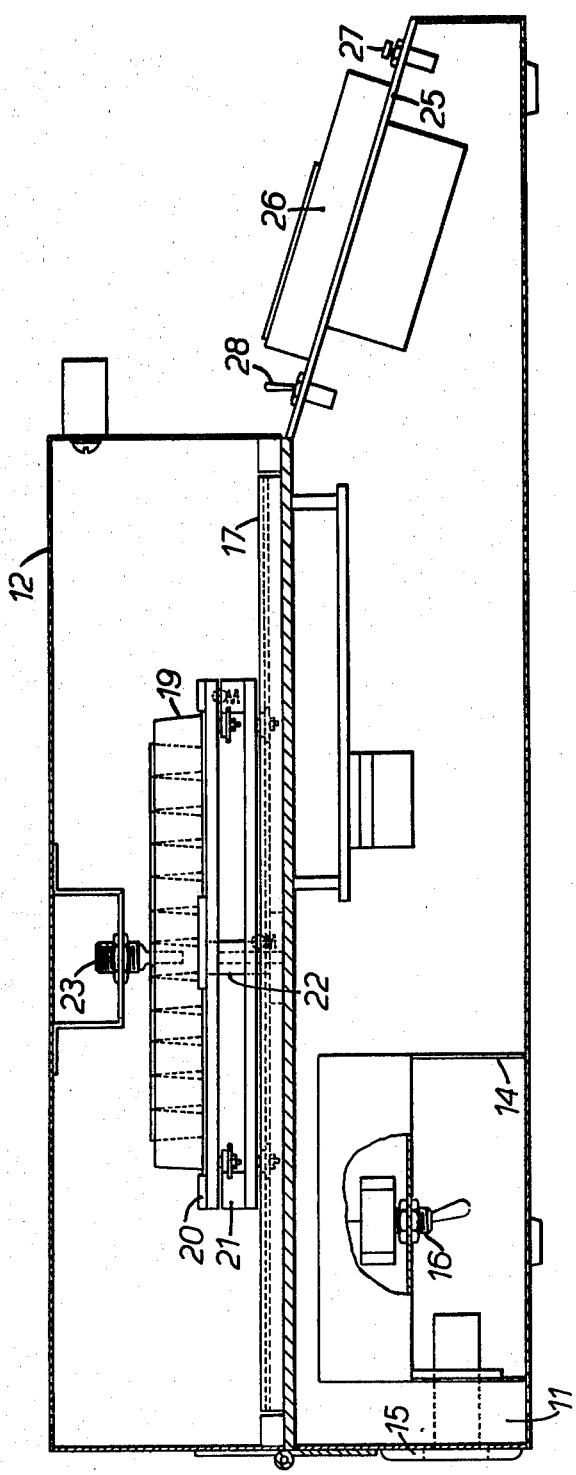
FIG. 1 is a sectional side view through a photometer according to the present invention.

FIG. 1 shows a sectional side view of a portable photometer which comprises a base housing 11 to which is hinged a light tight lid 12. The base housing 11 contains a source of power such as a battery (not shown) in a compartment 14. The battery may be of the rechargable type or facilities can be provided for supplying power from an external battery such as a vehicle battery. The housing 11 is also provided with a socket 15 to enable the photometer to be supplied with power from the mains via a built in adaptor. A change-over switch 16 is provided to effect a change in mains rating e.g. between 240 V and 110 V.

Rigidly mounted on top of the base housing 11 is a main base plate 17 on which is mounted a microtitre tray 19. The tray is movable in two directions at right angles to each other by virtue of the provision of an X-axis travel assembly 20 and a Y-axis travel assembly 21. A photodiode and collimator assembly 22 is also fixed to the base plate 17 under the tray 19 and in register with an L.E.D. and collimator assembly 23 adjustably mounted on the underside of the lid 12. The arrangement is such that in use the lid 12 is opened which withdraws the assembly 23 from a flat bottomed microtitre well of the tray 19. The tray is then moved to bring a different well into position above the assembly 22 and the lid is again closed which brings the assembly 23 into the different well to enable a measurement to be carried out on the solution in that well. FIG. 2 shows the operative arrangement from which it will be seen that the end of the assembly 23 dips into the test solution 24.

The electrical output from the photodiode of the assembly 22 is fed to a measuring circuit which is shown in more detail in FIG. 4 and will be described later. Suffice to say, the base housing 11 also provides a control panel 25 for the photometer, which control panel is not covered by the lid 12. Among other things on the control panel 25 is a meter 26, a push button 27 enabling the dark current to be set by a further control (not shown) and a switch 28 for enabling the battery to be recharged.

Referring now to FIG. 3, the L.E.D. and collimator assembly 23 is shown in more detail. It consists of a tubular housing 30, a portion of which is externally threaded to enable the assembly to be attached to the lid 12. The bore of the housing 30 is in two parts, a first portion 31 of the relatively large diameter and a second portion 32 of smaller diameter than the first. The whole of the second portion 32 and part of the first portion 31 are filled with a clear polyester resin to form a collimator for an L.E.D. 33 contained in the first portion 31. The L.E.D. abuts the end of the resin whose other end is polished to an optical finish. The remainder of the first portion 31 is filled with an epoxy encapsulant. This arrangement provides a rigid assembly which can withstand shock when the photometer is being moved. Preferably, the L.E.D. emits a red light because of the measurements that are presently contemplated but the wavelength of light may need to be different depending on the measurement to be performed, thus other colours of light can be provided by replacing the whole assembly.

Figure 4:
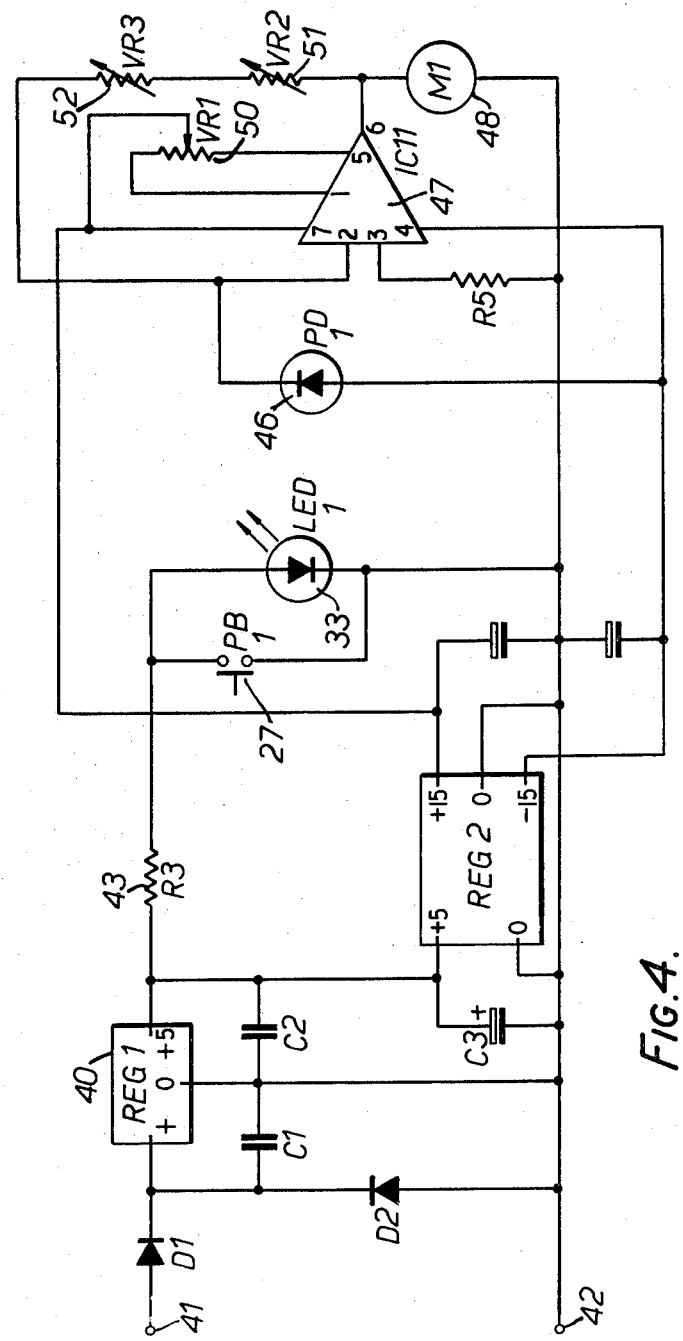
FIG. 4 is a circuit diagram of the measuring circuit of the photometer.

The major portion of the electrical circuitry is shown in FIG. 4. We have omitted the battery charging and mains adaptor circuitry as it is purely conventional.

A voltage regulator 40 is supplied with voltage from a power source (not shown) via input terminals 41, 42. The output from the regulator 40 is fed via a resistor 43 to the L.E.D. 33 which is shunted by a push button switch 27 for shorting out the L.E.D. to enable the dark current adjustment to be made.

The output from the regulator 40 also feeds a ±15 volt d.c. to d.c. converter 45 which is used to power the remaining circuitry consisting of the photodetector 46, an amplifier 47 and a meter 48.

Light from the L.E.D. 33 passes through a fixed path length of the solution being measured, through the diffuser and collimator and on to the photodiode 46 which is reverse biased and has a peak spectral response at 750 mm. The proportional leakage current from the photodiode 46 is amplified by the amplifier 47 which is an F.E.T. operational amplifier and drives the meter 48. A first variable resistor 50 is used to adjust the dark current when the push button 27 is pushed to short out the L.E.D., a second variable resistor 51 is used to adjust the zero absorbance setting of the meter 48 and a third variable resistor 52 is used to set the range of the meter 48.

The above description discloses the use of an L.E.D. as the light source. This is the most robust source available at present but other sources could be used, with suitable filtering, could expand the range of uses of the apparatus. At present, the above apparatus is particularly useful for the enzyme linked immunosorbent assay using blue solution.

Figure 5:
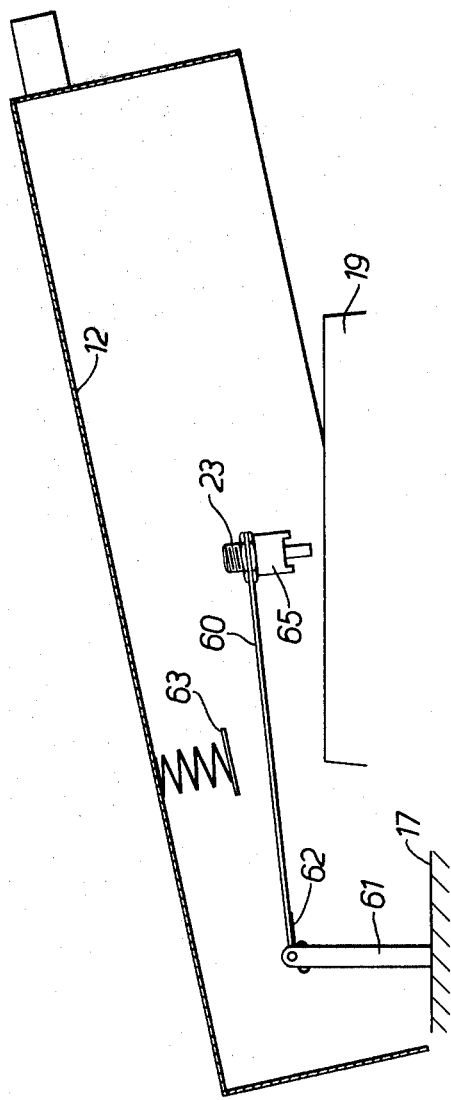
FIG. 5 is a diagrammatic side view of a portion of a further embodiment of the present invention.

FIG. 5 shows a diagrammatic side view of a modification to the above described apparatus. In this modification, it is only the arrangement for moving the L.E.D. and collimator assembly which differs, in all other respects the photometer is as described above and hence the same reference numerals will be used for the same parts.

The L.E.D. and collimator assembly 23 is removed from the lid of the photometer and located in an arm 60 which is pivotally mounted on a mounting 61 fixed to the base plate 17. The arm is spring biased in an upward direction in any convenient fashion, e.g. by means of a hair spring 62. The lid is provided with a spring abutment member 63 arranged to abut the arm 60 and force it down as the lid is closed so that, when the lid is closed the assembly 23 will be in position with the tip of the assembly 23 in the solution contained in a well of the tray 19 and the lid will be flush against the base plate 17 to ensure a light tight arrangement.

It has been found that it is preferrable to provide assembly 23 with a locating lense 65 which is adjustable with respect to the tip of the assembly 23. The purpose of the locating member is to engage the tray 19 adjacent the well of interest to compensate for any warping of the tray so that the life of the assembly 23 will always be the same distance from the bottom of each well even if the tray is warped. It may be necessary to use a castellated locating member 65.

It will be appreciated that the embodiment shown in FIG. 1 could be altered to spring load the assembly 23 in the lid 12 of the photometer if a locating member 65 were used.

We claim:

1. A portable photometer for measuring the transmission properties of a liquid contained in a container, comprising a base 11 having a lid 12 arranged to form a light tight enclosure therewith, a monochromatic light source 33 of fixed wavelength, a source of direct current 40 connected to said light source, a collimator assembly for said light source to form a collimated, narrow beam of light, a plurality of containers 19 each for a liquid sample 24 to be tested and each having a transparent bottom, a photodetecting device 46 positioned beneath said containers and arranged to receive said collimated, narrow beam of light, said plurality of containers 19 being movable with respect to base 11 to position a selected one of the containers in the light path between the light source 33 and the detecting device 46, the lid 12 being arranged to house the collimator assembly 23 and the plurality of containers 19, the collimator assembly 23 being provided with a locating member 65 and being resiliently coupled to said lid 12 so as to be movable in response to closure of the lid 12 from an inoperative position to an operative position where the end of the collimator assembly 23 projects into the sample 24 to be tested with the locating member 65 in contact with the top of the container whereby to locate the end of the collimator assembly 23 of a predetermined distance from the bottom of the container and so as to permit relative movement between the lid 12 and the collimator assembly 23 to ensure proper closure of the lid 12 when the collimator 23 is in contact with the top of the container.

2. A photometer according to claim 1, wherein the light source is a light emitting diode.

3. A photometer according to claim 2, wherein the diode emits red light.

4. A photometer according to claim 1, wherein said lid is provided with a depending member arranged to cause movement of said collimator assembly.

5. A photometer according to claim 1, wherein the photodetecting device is provided with a diffuser, the diffuser and the photodetecting device being mounted in an assembly so that the diffuser is spaced from the photodetecting device.

* * * * *